(12) United States Patent
Sarkar et al.

(10) Patent No.: US 10,724,076 B2
(45) Date of Patent: Jul. 28, 2020

(54) DE NOVO ENGINEERING OF SITE-SPECIFIC MOLECULES BY TETHERING

(71) Applicant: Regents of the University of Minnesota, Minneapolis, MN (US)

(72) Inventors: Casim Ali Sarkar, Minneapolis, MN (US); Igor Dodevski, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/725,991

(22) Filed: Oct. 5, 2017

(65) Prior Publication Data
US 2018/0094302 A1     Apr. 5, 2018

Related U.S. Application Data

(60) Provisional application No. 62/404,456, filed on Oct. 5, 2016.

(51) Int. Cl.
| | |
|---|---|
| *C12Q 1/6811* | (2018.01) |
| *C12Q 1/68* | (2018.01) |
| *C12Q 1/6823* | (2018.01) |
| *C12Q 1/00* | (2006.01) |
| *C07K 14/47* | (2006.01) |
| *C12Q 1/6834* | (2018.01) |
| *G01N 33/68* | (2006.01) |
| *C12N 15/10* | (2006.01) |

(52) U.S. Cl.
CPC ............ *C12Q 1/6811* (2013.01); *C07K 14/47* (2013.01); *C12N 15/1034* (2013.01); *C12Q 1/005* (2013.01); *C12Q 1/6823* (2013.01); *C12Q 1/6834* (2013.01); *G01N 33/6845* (2013.01); *C07K 2317/92* (2013.01); *C07K 2319/20* (2013.01); *C12N 15/1055* (2013.01)

(58) Field of Classification Search
None
See application file for complete search history.

(56) References Cited

U.S. PATENT DOCUMENTS

2002/0150947 A1* 10/2002 Erlanson .............. C07D 333/38
435/7.1

OTHER PUBLICATIONS

Erlanson et al. "Tethering: fragment-based drug discovery," Annu. Rev. Biophys. Biomol. Struct., 33:199-223, Jun. 2004.
Erlanson et al., "Site-directed ligand discovery," Proc. Natl. Acad. Sci. USA, 97(17):9367-9372, Aug. 2000.
Hanes and Plückthun, "In vitro selection and evolution of functional proteins by using ribosome display," Proc. Natl. Acad. Sci. USA, 94:4937-4942, May 1997.
Liu et al., "Optimized synthesis of RNA-protein fusions for in vitro protein selection" Meth. Enzymol., 318:268-293, 2000.
Odegrip et al., "CIS display: In vitro selection of peptides from libraries of protein-DNA complexes," Proc. Natl. Acad. Sci. USA, 101(9):2806-2810, Mar. 2004.
Plückthun, "Designed ankyrin repeat proteins (DARPins): binding proteins for research, diagnostics, and therapy," Annu. Rev. Pharmacol. Toxicol., 55:489-511, Jan. 2015.
Smith, "Filamentous fusion phage: novel expression vectors that display cloned antigens on the virion surface," Science 228(4705):1315-1317, Jun. 1985.
Zahnd et al., "Ribosome display: selecting and evolving proteins in vitro that specifically bind to a target," Nat. Methods, 4(3):269-279, Mar. 2007.

\* cited by examiner

*Primary Examiner* — Channing S Mahatan
(74) *Attorney, Agent, or Firm* — Fish & Richardson P.C.

(57) ABSTRACT

Materials and methods for specifically isolating and identifying biomolecules that bind to selected targets.

20 Claims, 9 Drawing Sheets

Specification includes a Sequence Listing.

N-cap
D L G K K L L D A A S A G Q D D E V R I L M A N G A D V N A  (SEQ ID NO:1)

Internal Repeat (IR):
D X X G X T P L H L A A X X G H L E I V D V L L A N G A D V N A S  (SEQ ID NO:2)

C-cap
Y X C G K T P F D L A I D N G N E D I A E V L Q K A A  (SEQ ID NO:3)

Randomized positions:
X(IR)    = A, E, G, K, L, M, P, Q, R, S, T, V, W         theoretical diversity: $3.7*10^5$
X(C-cap) = A, D, E, F, G, H, K, L, N, Q, R, S, T, V, W, Y  theoretical diversity: 16
Y(C-cap) = D, T                                           theoretical diversity: 2

FIG. 4

NH₂-MGGXXXXXXXGGCGGGSGG-tolA-COO (SEQ ID NO:4)

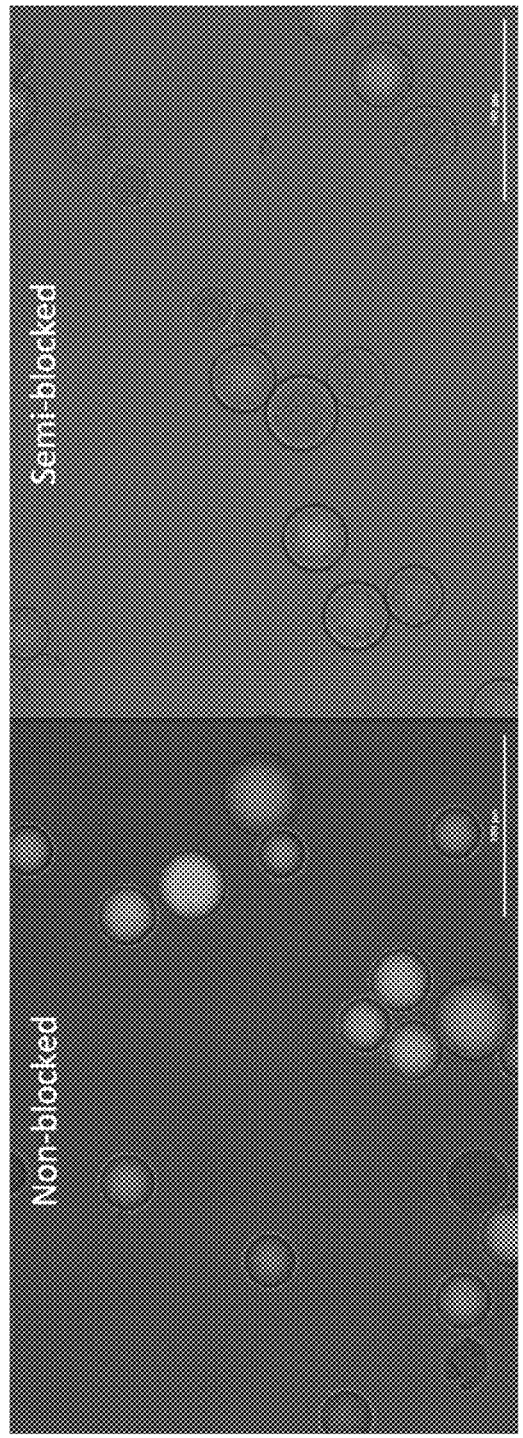

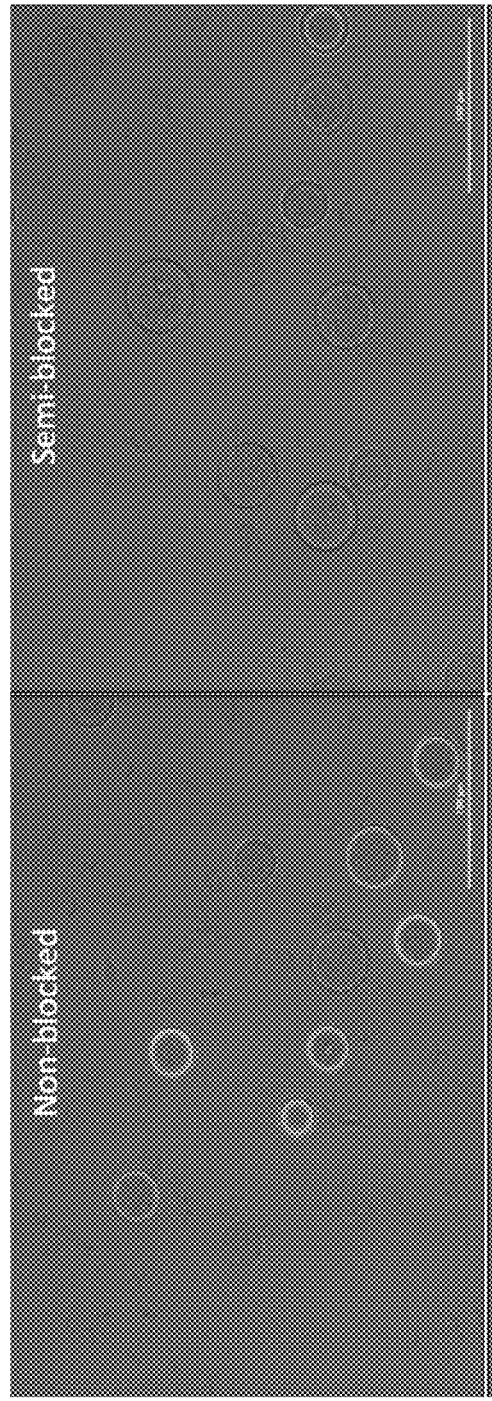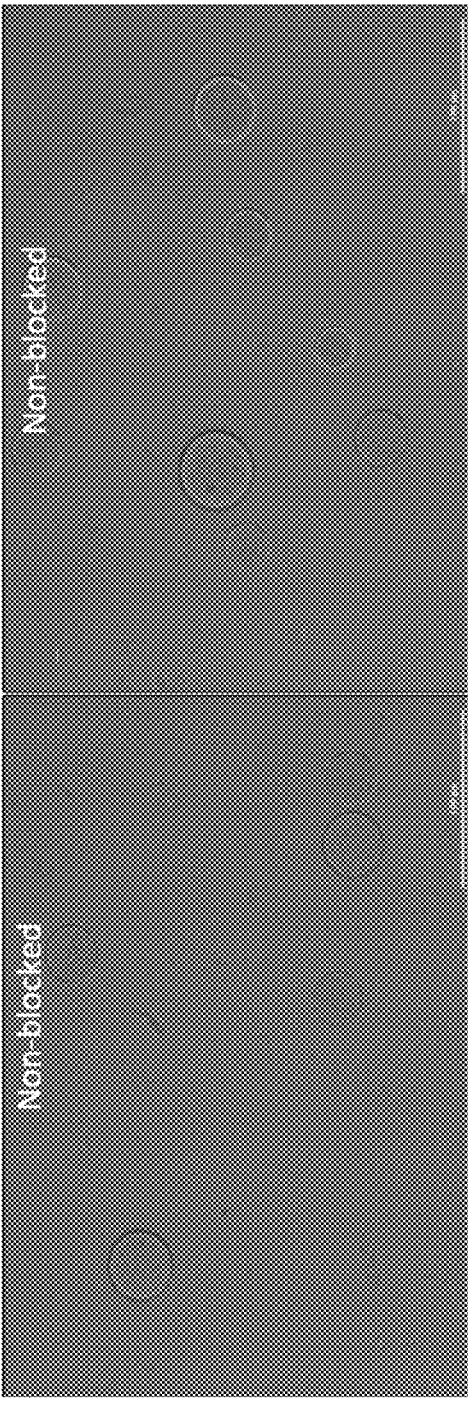
FIG. 8A  FIG. 8B  FIG. 8C  FIG. 8D

SEQUENCE LISTING

```
<160> NUMBER OF SEQ ID NOS: 4

<210> SEQ ID NO 1
<211> LENGTH: 30
<212> TYPE: PRT
<213> ORGANISM: Artificial Sequence
<220> FEATURE:
<223> OTHER INFORMATION: synthetic polypeptide

<400> SEQUENCE: 1

Asp Leu Gly Lys Lys Leu Leu Asp Ala Ala Ser Ala Gly Gln Asp Asp
1               5                   10                  15

Glu Val Arg Ile Leu Met Ala Asn Gly Ala Asp Val Asn Ala
            20                  25                  30

<210> SEQ ID NO 2
<211> LENGTH: 33
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (2)..(3)
<223> OTHER INFORMATION: Xaa can be Ala, Glu, Gly, Lys, Leu, Met, Pro,
      Gln, Arg, Ser, Thr, Val, or Trp
<220> FEATURE:
<221> NAME/KEY: misc_feature
<222> LOCATION: (5)..(5)
<223> OTHER INFORMATION: Xaa can be Ala, Glu, Gly, Lys, Leu, Met, Pro,
      Gln, Arg, Ser, Thr, Val, or Trp
```

```
<220> FEATURE:
<221> NAME/KEY: misc_feature
<222> LOCATION: (13)..(14)
<223> OTHER INFORMATION: Xaa can be Ala, Glu, Gly, Lys, Leu, Met, Pro,
      Gln, Arg, Ser, Thr, Val, or Trp

<400> SEQUENCE: 2

Asp Xaa Xaa Gly Xaa Thr Pro Leu His Leu Ala Ala Xaa Xaa Gly His
1               5                   10                  15

Leu Glu Ile Val Asp Val Leu Leu Ala Asn Gly Ala Asp Val Asn Ala
            20                  25                  30

Ser

<210> SEQ ID NO 3
<211> LENGTH: 27
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (1)..(1)
<223> OTHER INFORMATION: Xaa can be Asp or Thr
<220> FEATURE:
<221> NAME/KEY: misc_feature
<222> LOCATION: (2)..(2)
<223> OTHER INFORMATION: Xaa can be Ala, Asp, Glu, Phe, Gly, His, Lys,
      Leu, Asn, Gln, Arg, Ser, Thr, Val, Trp, or Tyr

<400> SEQUENCE: 3

Xaa Xaa Cys Gly Lys Thr Pro Phe Asp Leu Ala Ile Asp Asn Gly Asn
1               5                   10                  15

Glu Asp Ile Ala Glu Val Leu Gln Lys Ala Ala
            20                  25

<210> SEQ ID NO 4
<211> LENGTH: 20
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (4)..(12)
<223> OTHER INFORMATION: Xaa can be any naturally occurring amino acid

<400> SEQUENCE: 4

Met Gly Gly Xaa Xaa Xaa Xaa Xaa Xaa Xaa Xaa Gly Gly Cys Gly
1               5                   10                  15

Gly Ser Gly Gly
            20
```

DE NOVO ENGINEERING OF SITE-SPECIFIC MOLECULES BY TETHERING

CROSS-REFERENCE TO RELATED APPLICATIONS

This application claims benefit of priority from U.S. Provisional Application Ser. No. 62/404,456, filed on Oct. 5, 2016.

STATEMENT AS TO FEDERALLY SPONSORED RESEARCH

This invention was made with government support under CA179180 awarded by the National Institutes of Health. The government has certain rights in the invention.

TECHNICAL FIELD

This document relates to materials and methods for isolating and identifying biomolecules (e.g., DNA, RNA, polypeptides, and aptamers), as well as DNA encoded small molecules, that can bind to selected targets. In particular, the methods provided herein include the use of libraries of molecular entities that are DNA-tagged and thus selectable.

BACKGROUND

The biological activity of a polypeptide often is highly dependent on the specific target epitopes with which it interacts. Examples of polypeptide action include inhibition of an enzyme by targeting the enzyme's active site, blocking a mitogenic factor by competing for its receptor binding site, and targeting site-specific mutations that arise in diseases such as cancer. The development of specifically targeted therapeutics, such as engineered proteins that can discriminate between single mutations, can be essential for targeting disease-associated mutant proteins, without affecting normal proteins. This has proven to be an extremely difficult problem to solve, however, to the extent that some protein mutants have been considered undruggable.

SUMMARY

Biomolecule-inspired therapeutics (e.g., peptides, proteins, macrocycles, and nucleic acids) can provide greater affinities and specificities than many small molecules, but there currently are no robust experimental methods to ensure de novo development of biomolecules with affinity for a specific site on a target molecule. This document provides, inter alia, tethering methods (e.g., Tethering ribosome display (RD) methods) that are based, at least in part, on the discovery that reversible intermolecular disulfide bonds between cysteine-containing targets and polypeptides in a cysteine-containing polypeptide library can be leveraged to selectively enrich for polypeptides near the target cysteine. The approaches described herein can be used to enrich for biomolecules (e.g., nucleic acids or polypeptides) or small molecules that are target-site specific. In some cases, display technologies such as RD, mRNA display, or phage display can be used. The ultimate goal of the methods provided herein is to facilitate the de novo identification of biologics and chemistries characterized by pharmacologically desirable features, such as higher binding affinity, better target selectivity, and binding to predefined allosteric sites on a target.

In one aspect, this document features a method for enriching for a molecule that binds to a target molecule. The method can include (a) contacting the target molecule with a population of candidate binding partners, where each candidate binding partner is coupled to a unique nucleic acid tag, each candidate binding partner further includes or is coupled to a first tethering partner, the target molecule is coupled to a second tethering partner, and the contacting is under conditions in which the first and second tethering partners interact to promote binding between the target molecule and a candidate binding partner that specifically binds to the target molecule, and (b) separating at least one candidate binding partner bound to the target molecule from candidate binding partners not bound to the target molecule. The population of candidate binding partners can include polypeptides, nucleic acids, aptamers, or small molecules. The unique nucleic acid tag can be a DNA tag. When the unique nucleic acid tag is a DNA tag, the method can further include identifying the at least one candidate binding partner based on the sequence of the DNA tag. The unique nucleic acid tag can be an mRNA tag. When the unique nucleic acid tag is an mRNA tag, the method can further include identifying the at least one candidate binding partner based on reverse transcription of the mRNA tag, and sequencing of cDNA resulting from the reverse transcription. The first tethering partner can be a first cysteine residue within each candidate binding partner, the second tethering partner can be a second cysteine residue within the target molecule, and the first and second cysteine residues can interact to form a disulfide bond when a candidate binding partner has inherent affinity for the target molecule. The first tethering partner can be a first biomolecule coupled to the candidate binding partners and the second tethering partner can be a second biomolecule coupled to the target molecule, and the first and second tethering partners can interact when a candidate binding partner has inherent affinity for the target molecule. The first tethering partner can be a first synthetic molecule coupled to the candidate binding partners and the second tethering partner can be a second synthetic molecule coupled to the target molecule, and the first and second tethering partners can interact when a candidate binding partner has inherent affinity for the target molecule. The method can include the use of a display technique (e.g., ribosome display, mRNA display, phage display, covalent DNA display, CIS display, STABLE, or microbead display). The target molecule can be a polypeptide (e.g., a polypeptide with a length of 10 to 50 amino acids, or 50 to 100 amino acids).

In another aspect, this document features a method for enriching for a binding partner for a target molecule, where the method can include (a) contacting (i) a population of ternary complexes comprising ribosomes associated with (1) mRNA in vitro transcribed from a DNA library that encodes a library of candidate binding partners, and (2) in vitro translated products synthesized by the ribosomes from the mRNA, wherein the in vitro translated products include a first tethering partner, and (ii) a target molecule including a second tethering partner, under conditions in which the first and second tethering partners interact to promote binding between the target and a candidate binding partner that specifically binds to the target, and (b) separating one or more ternary complexes bound to the target molecule from ternary complexes not bound to the target molecule. The method can further include identifying the binding partner within the one or more ternary complexes, based on reverse transcription of the mRNA and sequencing of cDNA resulting from the reverse transcription.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is the amino acid sequence (SEQ ID NO:4) of a second generation Tethering RD library based on a fully randomized peptide scaffold. The amino acid sequence shows randomized positions as X, and the single cysteine for tethering is underscored. The peptide library with nine consecutive randomized amino acids is designed for high molecular diversity ($3 \times 10^{11}$ individual sequences), and the cysteine is located in a structural flexible region to increase the propensity of disulfide bond formation.

FIGS. 7A and 7B are pictures showing selective blocking with free biotin of streptavidin (SA) binding sites in the outer shell of SA-SEPHAROSE® beads. A defined concentration of beads is first incubated with either 0 μM (FIG. 7A) or 18 μM (FIG. 7B) free biotin, and then incubated with biotinylated wt MBP for protein pull down. The protein was pre-labeled on its N-terminus with Alexa555-NHS dye for fluorescence imaging. The concentration of free biotin used in the experiment of FIG. 7B was optimized to block about half of the total SA binding sites. SA binding sites in the outer shell but not in the core of the beads were blocked, and core sites remained available for pull-down of excess biotinylated target protein. Due to the 4 MDa molecular size exclusion limit of the SEPHAROSE® resin, blocking the SA sites on the outer shell of the beads should preclude binding of positive ribosomal ternary complexes after the panning step of a round of Tethered-RD. The pictures show an overlay of two images taken in the brightfield and the RFP channels.

FIGS. 8A-8D are a series of pictures showing that semi-blocked SA-SEPHAROSE® beads exhibit low binding capacity for biotinylated ternary ribosomal complex. Ribosomal complexes displaying a biotinylated SNAP-sfGFP fusion protein (acting as a proxy for positive clones in Tethered RD) were incubated with unblocked (FIG. 8A) or semi-blocked (FIG. 8B) beads. Binding of biotinylated ribosomal complex as evidenced by sfGFP signal was markedly reduced for semi-blocked beads (FIG. 8B) compared to unblocked beads (FIG. 8A). To demonstrate the presence of excess unbound biotinylated complexes in the supernatant of semi-blocked beads (FIG. 8B), the supernatants of both FIGS. 8A and 8B were pulled down with unblocked beads, and the results are shown in FIGS. 8C and 8D, respectively. The stronger signal on the beads in FIG. 8D compared to FIG. 8C demonstrates a larger amount of biotinylated complexes in the supernatant of FIG. 8B compared to FIG. 8A. The pictures show an overlay of two images taken in the brightfield and the GFP channels.

DETAILED DESCRIPTION

This document features materials and methods for using tethering to facilitate the identification of molecules having affinity for a specific site on a target, particularly where the candidate molecules are nucleic acid molecules, or are molecules linked to a DNA tag that can be decoded to identify the associated candidate. In some embodiments, the methods disclosed herein can include the use of display techniques. For example, this document is based, at least in part, on the discovery that reversible intermolecular disulfide bonds between cysteine-containing targets and polypeptides in a cysteine-containing polypeptide library expressed via RD can be used to selectively enrich for polypeptides near the target cysteine, followed by identification of the polypeptides via reverse transcription. The methods described herein can be used to enrich for biomolecules (e.g., nucleic acids or polypeptides), or for small molecules that are target-site specific.

RD is an example of a powerful in vitro selection method for the engineering of protein-based high-affinity binders to targets of interest, using in vitro protein evolution to generate proteins that can bind to a selected ligand. The process uses complexes containing translated polypeptides that are associated with their mRNA progenitor via a ribosome, to bind to the ligand of interest. mRNA in the complexes that bind well are then reverse transcribed to cDNA, and their sequences are amplified by PCR, resulting in nucleotide sequence(s) that can be used to create tightly binding proteins.

Figure 1:
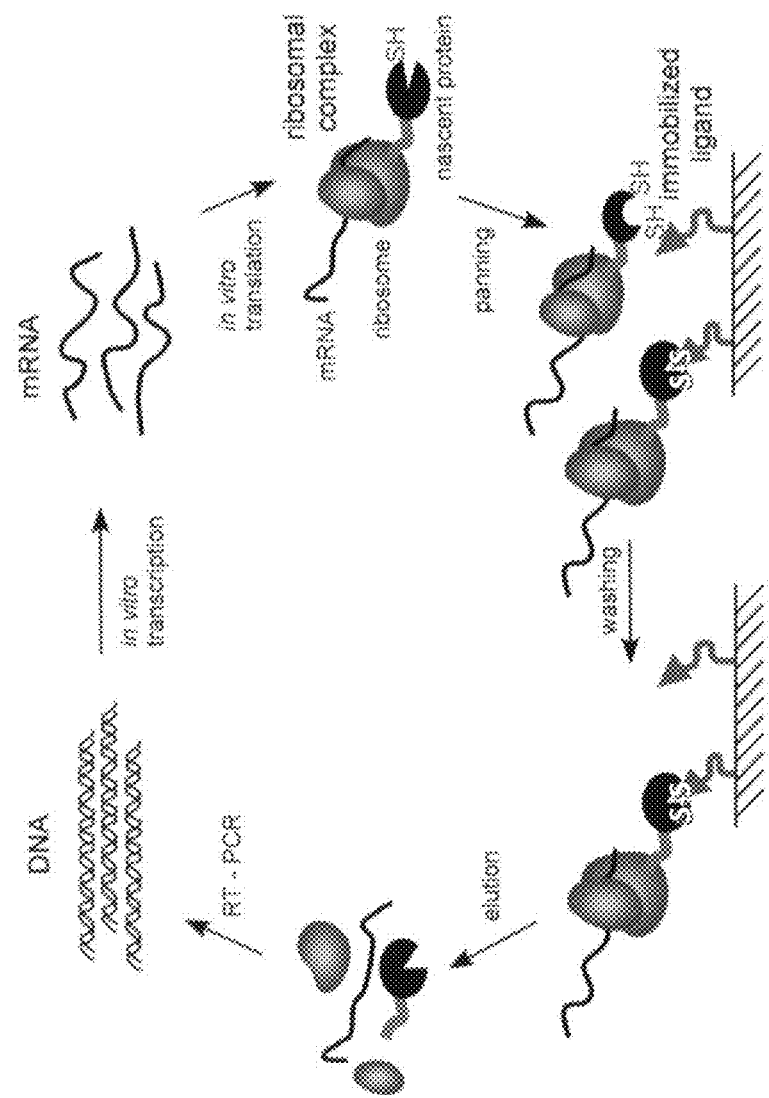
FIG. 1 is a schematic of a Tethering RD round, showing the sulfhydryl groups of the cysteines used for tethering.

Methods for carrying out RD are known in the art; methods described elsewhere typically include some of the steps set forth in Example 1 and FIG. 1 herein. In general, RD begins with a library of DNA sequences encoding a library of polypeptides. The DNA library is in vitro transcribed, and then in vitro translated. Because sequences in the DNA library are fused to a spacer sequence lacking a stop codon before its end, release factors are prevented from binding and triggering disassembly of the translational complex. Thus, the spacer sequence remains attached to the peptidyl tRNA and occupies the ribosomal tunnel, permitting the translated polypeptide to protrude from the ribosome and fold. This yields a complex of mRNA, ribosome, and polypeptide that can bind to a ligand. In some cases, the ternary complex can be stabilized by the lowering of temperature and/or adding cations such as $Mg^{2+}$.

The complexes are then subjected to binding or "panning" steps, in which they are introduced to ligand that typically is attached to a surface. Panning can be accomplished using, for example, an affinity chromatography column with a resin bed containing ligand, a 96-well plate with immobilized surface-bound ligand, or magnetic beads coated with ligand. Complexes that bind well are immobilized and subsequently eluted (e.g., by high salt concentration, chelating agent(s), or mobile ligand(s) that complex with the binding motif of the protein and allow dissociation. In some cases, the mRNA from the bound complexes then can be reverse transcribed into cDNA, mutagenized, and iteratively used again in further RD rounds with greater selective pressure to isolate even better binders.

A heretofore unresolved challenge in de novo engineering of binders by RD, however, is to direct the biomolecular discovery process to predefined epitopes on a target protein, such as allosteric sites with potential pharmacological value. This document provides materials and methods for site-specific selection of molecules that can bind to a particular target with high spatial precision and experimental ease, through the inclusion of tethering partners that can enhance and/or facilitate interactions between a target and molecules that specifically recognize the target.

Thus, in some embodiments, this document provides systems for Tethering-RD. In some cases, the systems can include (1) DNA sequences encoding (2) a library of biomolecules (e.g., polypeptides containing natural and/or unnatural amino acids) that result from ribosomal synthesis, (3) ribosomes for in vitro translation of the library, (4) a selected target molecule that can be coupled to a solid support, and (5) first and second tethering partners linked, respectively, to the library members and to the target molecule.

The DNA library used for Tethering RD can encode a population of potential binding partners for the target of interest. The candidate binding partners can be any type of biomolecule that can be DNA-encoded and ribosomally-synthesized. In such cases, a library of candidate binding partners can include polypeptides (which also may be referred to as peptides or proteins), for example. The candidate molecules in a library can have lengths ranging from about one amino acid (aa) to about 1000 aa or more, or any range there between (e.g., one to 10 aa, 10 to 20 aa, 20 to 30 aa, 30 to 50 aa, 50 to 100 aa, 100 to 200 aa, 200 to 500 aa, 500 to 1000 aa, or more than 1000 aa). Polypeptides in a library can include natural amino acids (those that acids are naturally incorporated into polypeptides, including alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, and selenocysteine), non-natural amino acids (e.g., DL-7-azatryptophan, DL-hydroxy-norvaline, L-canavanine, quisqualic acid, p-bromo-DL-phenylalanine, β-fluoro-L-tyrosine, 1-amino-1-cyclopentane carboxylic acid, L-threo-β-hydroxy aspartic acid, L-thiazolidine-4-carboxylic acid, β-t-butyl-DL-alanine), or a combination thereof.

In some embodiments, a library of candidate binding partners for use in a Tethering RD method can exploit a polypeptide architecture based on modular repeats, such as when DARPins are used as the source for macromolecular diversity (Plückthun, *Annu. Rev. Pharmacol. Toxicol.* 55:489-511, 2015). See, for example, Example 2 herein, and also FIG. 2, which sets forth the general structure of a DARPin molecule and provides sequences that can be randomized to generate a library of candidates. As described below, the candidate binding partners for the target contain tethering components that, in some cases, can be cysteine residues. In such cases, a site-specific, reversible disulfide bond tether can be formed between ribosome-displayed DARPins and target proteins. This can allow for the selective enrichment of otherwise undetectable, transient, and low-affinity binding interactions between a DARPin and the target, because even modest bimolecular interaction entropically stabilizes the disulfide bond under partially oxidizing conditions. Initial DARPin-based hits can serve as building blocks that can be engineered into site-specific, high-affinity binders by increasing the number of sequence-diversified repeats in the displayed DARPins and using a standard RD selection method under tether-free conditions.

In some embodiments, a DNA library can encode candidate binding partners that are more fully randomized polypeptides, containing sequences of consecutive randomized amino acids. See, for example, Example 3 and FIG. 4 herein. Using more fully randomized candidates can increase the level of diversity of the library. The randomized segment within such binding partners can have a length between 1 aa and 100 aa or any range there between (e.g., 1 to 3 aa, 2 to 5 aa, 5 to 10 aa, 10 to 15 aa, 15 to 20 aa, 20 to 25 aa, 25 to 30 aa, 30 to 40 aa, 40 to 50 aa, 50 to 75 aa, or 75 to 100 aa).

The ribosomes used in the systems and methods provided herein can be commercially obtained in standard in vitro translation kits, for example.

The target molecules used in the Tethering RD methods provided herein can be any molecule that can be linked to or include a molecular tether, and that can be bound by a ribosomally-synthesized partner, and in some cases, also can be coupled to a solid support. In some embodiments, for example, a selected target molecule can be a full length protein, or a fragment of a protein (e.g., a polypeptide containing a particular epitope or domain of a protein). Methods for generating particular proteins and polypeptides of interest include those known in the art. Methods for coupling polypeptides to a solid support also are known in the art, and include, for example, biotin-streptavidin interaction or covalent coupling of amino groups to immobilized carboxylic acid groups via N-hydroxysulfosuccinimide/1-ethyl-3-(3-dimethylaminopropyl) carbodiimide (sNHS/EDC) chemistry.

The target molecules and the members of the library of candidate binding partners include, or are linked to, respectively, first and second tethering partners that can interact with each other to facilitate the interaction between the target and a ribosomally-synthesized binding partner that specifically recognizes the target. In some embodiments, the first and second molecular tethers can be cysteine residues present in the target and in the displayed library. These cysteines can interact to form disulfide bridges as indicated, for example, in FIG. 1. Such cysteine residues can be inserted into the sequence of a target or a DNA-encoded library using engineering and mutagenesis methods that are known in the art, for example. In some cases, the molecular tethers can be biomolecules or synthetic molecules, (e.g., azide-alkyne pairs, or other click chemistry pairs). While not being bound by a particular mechanism, the interaction between two tethering partners is not likely to be sufficient, on its own, to result in efficient formation of a complex between a target and a library member unless the library member also has inherent affinity for the target. The interaction between two tethering partners can, however, enhance the specific interaction between a target and a binding partner within the library. In instances when the tether does form efficiently in the absence of inherent affinity of the library member, the tether can be selectively weakened by changing the buffer (e.g., by addition of dithiothreitol to partially reduce disulfide bonds), thus imparting a selective pressure to more strongly enrich for library members that exhibit binding affinity for the target near the tether.

This document also provides Tethering RD methods that include the use of molecular tethers with RD protocols. In general, the methods provided herein can include steps used in standard RD procedures, with modifications that allow for the formation of specific tethering bonds between the displayed protein library and the target. For example, the methods provided herein can include the steps set forth in Example 1 below. These can include some or all of the following steps: obtaining or generating a DNA library encoding a library of candidate molecules, where each member of the library contains or is linked to a first tethering partner; amplifying the DNA library; subjecting the DNA library to in vitro transcription; in vitro translating the mRNA resulting from the in vitro transcription; contacting the ribosome/mRNA/product complexes with a target molecule containing or linked to a second tethering partner that can interact with the first tethering partner; pulling down ribosome/mRNA/product complexes that bind to the target; washing the pulled-down complexes; and reverse transcribing the mRNA from the pulled down complexes. The resulting cDNA can then be sequenced to identify the encoded binding partner(s) for the target. In some cases, the cDNA can be subjected to one or more further rounds of RD, with or without mutagenesis, and with or without the use of molecular tethering partners.

In some cases, the steps of a Tethering RD method can be adjusted to include additional or alternative features, such as those described in Example 3 below. For example, the concentration of the target used in the panning step can be adjusted (e.g., increased) to enhance the enrichment of bound partners. Increasing the concentration of the target protein can, for example, increase the rate of formation of the tether between the displayed polypeptides and the target. It is noted, however, that the amount of target protein may be limited by factors such as the requirement for matching amounts of immobilized affinity support (e.g., immobilized streptavidin to bind biotin) to pull down both tethered and non-tethered target following the panning step, and that increasing the target concentration of Cys-containing, biotinylated targets could increase the formation of disulfide bond-linked target dimers with two biotin moieties, which might act to cross link individual paramagnetic beads and result in their aggregation. These potential issues can be circumvented, however. For example, in some embodiments, a method can include using high capacity streptavidin-SEPHAROSE® beads (e.g., beads with covalently immobilized streptavidin) to selectively sequester free target but not the target tethered to ternary complexes. Supernatants containing tethered and non-tethered ternary complexes can be treated with streptavidin magnetic beads to pull down positive ternary complexes and separate them from non-tethered complexes. In some cases, streptavidin-SEPHAROSE® beads can be partially pre-blocked on their outer surface with free biotin, allowing free biotinylated targets (e.g., target dimers) to be absorbed into the core of the beads while the 2 MDa ternary complexes are prohibited from binding and remain in the supernatant. See, e.g., Example 3 and FIGS. 7A and 7B herein.

In some embodiments, excess reducing agent and/or small molecular weight sulfhydryl groups can be removed from the library after translation, before panning it against the target. For example, diafiltration of translated ternary ribosomal complexes can be used to remove excess reducing agent.

Figure 5:
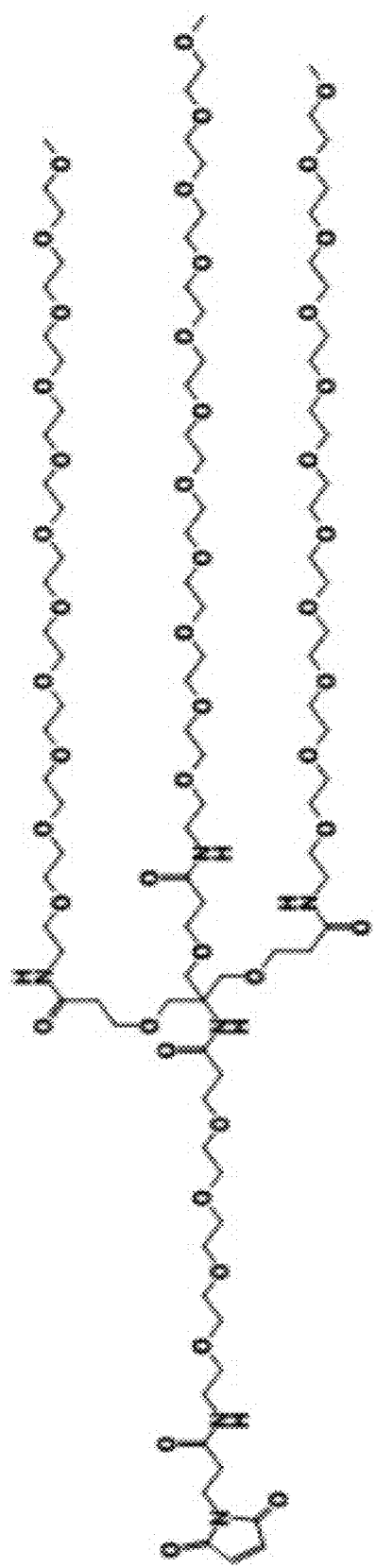
FIG. 5 is the chemical structure of maleimide-dPEG4-(m-dPEG$_{11}$)$_3$ (malPEG) used to block the free surface cysteines on ribosomes. The branched molecule can increase the hydrodynamic radius of the molecule to limit its reactivity toward sulfhydryls located in the core of the ribosome. The compound has a MW of 228.59, and the single compound dPEG® spacer contains 64 atoms and has an average size of 75.8 Å.

In some embodiments, the Tethering-RD methods provided herein can include one or more steps for blocking free Cys residues on the surface of the ribosomes. Such blocking can prevent the free surface cysteines from forming non-specific disulfide bonds with target molecules, for example. In some cases, a compound such as maleimide-dPEG4-(m-dPEG11)3 (malPEG; FIG. 5) can be used to block free surface cysteines on the ribosomes. As described in Example 3 and indicated by the data shown in FIG. 6, ribosomes blocked with malPEG can fully retain the ability to translate protein.

It is to be noted that the systems and methods described herein can be extended beyond polypeptides to other types of biomolecules (e.g., DNA, RNA, and/or aptamers) or even to small molecules, which do not require the use of ribosomes. For example, a library of DNA molecules incorporating or linked to a first tethering partner can be synthesized, amplified, and tested against a target molecule that incorporates or is linked to a second tethering partner, where the target molecule is immobilized on a solid support to allow for separation of target-binding partner complexes from unbound targets and unbound members of the library. In some cases, a library of candidate DNA molecules can be transcribed, and the resulting mRNAs—which can be linked to or contain a first tethering partner—can be tested for binding to a target.

Polypeptide or polynucleotide aptamers also can be used in the systems and methods provided herein. These molecules can be generated by selecting them from a large random sequence pool, although natural aptamers also exist. Aptamers are folded, single-stranded nucleic acids or folded polypeptides with activities that, like folded proteins, depend on their three-dimensional shapes and surface features. The use of aptamers can provide benefits that may include small size, chemical stability, ease of synthesis, lack of immunogenicity, and, their utility in in vitro selection technology as described herein. In some embodiments, a random library containing $10^{14}$ or more aptamer candidates can be used, providing diversity that can exceed that encoded in mammalian systems, for example. Methods that include the use of a nucleic acid aptamer library do not involve any ribosomes or a translation step. In these methods, a library of single-stranded DNA or RNA biomolecules can be functionalized with one portion of the tether and then panned against the target. Aptamers that bind can be directly amplified by PCR (for DNA aptamer libraries) or RT-PCR (for RNA aptamer libraries).

The candidate molecules in a nucleic acid library (e.g., a DNA, RNA, or nucleic acid aptamer library) can have lengths ranging from about ten nucleotides (nt) to about 1000 nt or more (e.g., 10 to 20 nt, 20 to 30 nt, 30 to 50 nt, 50 to 100 nt, 100 to 200 nt, 200 to 500 nt, 500 to 1000 nt, or more than 1000 nt). When a library includes polypeptide aptamers, the aptamers can have a length ranging from about one aa to about 1000 aa or more (e.g., 10 to 20 aa, 20 to 30 aa, 30 to 50 aa, 50 to 100 aa, 100 to 200 aa, 200 to 500 aa, 500 to 1000 aa, or more than 1000 aa).

Also useful in the methods provided herein are DNA-encoded small molecule libraries (DELs). DELs are libraries of small molecules, where each molecule in the library is covalently linked to a specific and unique DNA tag that can be decoded by sequencing to reveal the identity of the linked small molecule. This can allow for drug discovery approaches that fall into the category of "selection" rather than simply "screening." DEL-based techniques thus can be considered as a cross-over between the selection/biologics world and screening/small molecule world. The use of DELs in tethering molecular affinity selection can give rise to orders of magnitude larger libraries that can be assayed, as compared to standard small molecule libraries. As for the other libraries utilized in the systems and methods disclosed herein, the candidate binding partners in a DEL can be linked to a first tethering partner that binds to a second tethering partner on a target molecule, particular when a particular candidate binding part has inherent affinity for the target.

In addition, the methods described herein can extend beyond RD to other types of display technologies. Such methods can include the use of, without limitation, mRNA display, phage display, covalent DNA display, CIS display, STABLE, and microbead display.

In some cases, for example, RNA display can be used in a tethering method as provided herein. In particular, mRNA display is a technique that can be used for in vitro peptide evolution of molecules that can bind to a desired target. Like RD, the process results in translated polypeptides that are associated with their mRNA progenitor, but they are associated via a puromycin linkage rather than via a ribosome. Puromycin is an analogue of the 3' end of a tyrosyl-tRNA, and has a structure that mimics both adenosine and tyrosine. Unlike the cleavable ester bond in a tyrosyl-tRNA, however, puromycin has a non-hydrolyzable amide bond, such that the puromycin interferes with translation and causes premature release of translation products. It is noted that other factors (e.g., oligonucleotides and/or other spacers) can be included along with puromycin to provide flexibility and a suitable length for the puromycin to enter the A site of the ribosome. See, e.g., Liu et al., *Meth. Enzymol.* 318:268-293, 2000. The mRNA-polypeptide complexes can incorporate or be linked to a first tethering partner (e.g., a Cys within the sequence of the encoded polypeptide, or another biomolecule or synthetic molecule). The library of mRNA-polypeptide fusions then be introduced to an immobilized target in a selection step (e.g., affinity chromatography) where, again, the target contains or is coupled to a second tethering partner. As in the Tethering RD methods described herein, the puromycin-linked mRNA-polypeptide complexes that bind well can then be reverse transcribed to cDNA and amplified, yielding a nucleotide sequence encoding a polypeptide with high affinity for the target of interest.

In some cases, the tethering methods provided herein can utilize phage display, which provides another platform for connecting polypeptides with nucleic acids by which they are encoded, using bacteriophages—viruses that infect bacteria. See, e.g., Smith, *Science* 228(4705):1315-1317, 1985. In general, a library of nucleic acids encoding candidate binding molecules can be inserted into bacteriophage DNA at the site of a phage coat protein gene, causing each phage to express and "display" a polypeptide on its outer surface while still containing the coding sequence for the polypeptide within, resulting in a connection between the nucleic acid (genotype) and the expressed polypeptide (phenotype). The displaying phages can be screened against a target molecule (e.g., a polypeptide containing a particular epitope, or a DNA molecule) to detect interactions between the target and particular displayed polypeptides. Again, the expressed and displayed polypeptides can incorporate or be linked to a first tethering partner (e.g., a Cys within the sequence of the encoded polypeptide), and the target can be linked to a second tethering partner, such that interactions between the first and second tethering partners, coupled with interactions between the displayed polypeptide and the target themselves, result in specific binding. Bacteriophage DNA from samples that bind well can then be reverse transcribed to cDNA and amplified, giving a nucleotide sequence that encoding a polypeptide with high affinity for the target of interest.

Another suitable display platform is CIS display, which provides an in vitro selection system that utilizes the ability of the RepA DNA replication initiator protein to bind to the template DNA from which it is expressed (referred to as "cis-activity"). See, e.g., Odegrip et al., *Proc. Natl. Acad. Sci. USA* 101(9):2806-2810, 2010. With CIS display, a peptide library can be created by linking DNA fragments with random sequences to a DNA encoding RepA. In vitro transcription and translation can be performed, resulting in a pool of polypeptide-DNA complexes in which each polypeptide is stably associated with its encoding DNA. A first tethering partner (e.g., a Cys residue) can be included in the encoded polypeptides, or can be otherwise coupled to the encoded polypeptides (e.g., when the first tethering partner is another biomolecule or a synthetic molecule). The complexes then can be introduced to the target of interest as described herein, and ligands with inherent affinity for the target can be selected.

The invention will be further described in the following examples, which do not limit the scope of the invention described in the claims.

EXAMPLES

Example 1—Tethering RD Protocol

In general, Tethering RD methods carried out as described herein included the following steps.

1. PCR Amplification of DNA Library:

To amplify a DNA library, reaction conditions were scaled to achieve a desired library diversity. The library contained a T7 promoter region and a TolA region.

|  | 1x |
|---|---|
| 5x HF buffer | 10 |
| RD_T7_for (10 μM) | 2.5 |
| RD_tolAk_rev (10 μM) | 2.5 |
| dNTPs (10 mM each) | 1.0 |
| DNA template | X |
| Phusion hot start polymerase | 0.5 |
| UHP | X |
| total | 50 |

| PCR cycling program | |
|---|---|
| 30 sec | 98° C. |
| 10 sec | 98° C. |
| 15 sec | 65° C. |
| 30 sec | 72° C. |
| 5 min | 72° C. |
| ∞ | 4° C. |

Amplification was carried out for 25 cycles, and reactions were verified by agarose gel electrophoresis. The reaction was cleaned up using the PCR clean up kit from NEB, and DNA was quantified based on $A_{260}$.

2. In Vitro Transcription:

The following reagents were mixed in the following order on ice, and transcription was carried out for 3 hours at 37° C.

|  | 1x |
|---|---|
| UHP | X |
| purified PCR product (2000 ng) | X |
| 5x homemade T7 transcription buffer | 20 |
| NTPs (25 mM of each) | 12 |
| RNasin Plus | 2 |
| T7 RNA polymerase (NEB) | 4 |
| total | 100 |

3. RNA Isolation:

The following steps were performed on ice. To 100 μl of transcribed RNA, 300 μl ice-cold UHP and 400 μl 6 M LiCl were added, and incubated on ice for 30 minutes. Samples were spun at 20,000 g, 4° C. for 30 minutes (the pellet is visible after 1 minute). The supernatant was removed with a pipette (10-20 μl typically remained in the tube). The pellet was washed with 500 μl ice-cold 70% EtOH by adding the solution and then removing it. Visible pellets that became dislodged typically settled readily. The pellet was solubilized in 200 μl ice-cold UHP by gentle pipetting until visible clumps disappeared. The solution was left on ice for 10 minutes and then pipetted again. Solubilization required varying lengths of time. Samples were spun at 20,000 g, 4° C. for 5 minutes, which may or may not have resulted in a visible pellet. After transferring 180 μl of the supernatant to a new tube, 20 μl of 3 M NaOAc was added, followed by 500 μl ice-cold 100% EtOH. Samples were incubated at −20° C. for 30 minutes or overnight, then spun at 20,000 g, 4° C. for 30 minutes. A brownish translucent pellet was sometimes visible. The supernatant was discarded and the pellet was washed with 500 μl ice-cold 70% EtOH. The supernatant was then discarded with a pipette. Most of the liquid could be removed without disturbing the pellet. The tube was placed at 37° C. for 15 minutes to evaporate most, but not all, of the solution. The pellet was then solubilized in 20 μl ice-cold UHP, and a 1:10 dilution in UHP (1 μl mRNA into 9 μl ice-cold UHP) was used for $A_{260}$ quantification. The remaining mRNA was immediately N2 frozen. The target mRNA typically was at least 5000 ng/μl for a ~500 nucleotide construct.

4. Blocking of Ribosomes:

Free cysteine residues on ribosomal surface were blocked with sulfhydryl-reactive maleimide-dPEG$_4$-(m-dPEG$_{11}$)$_3$ (malPEG). This step can be performed ahead of time and blocked ribosomes can be snap-frozen in liquid N2. Purified ribosomes (33 μl; one vial of NEB ribosomes, cat. # P0763S) were thawed on ice for 20 minutes and then mixed with 33 μl 20 mM malPEG (2229 g/mol). To prepare 20 mM malPEG, 4.6 mg malPEG was dissolved in 103 μl−5 μl=98 μl ice cold ribosome buffer (20 mM HEPES-KOH pH 7.6, 30 mM KCl, 10 mM MgAc, w/o BME), and incubated on ice for 1 hour. Unreacted maleimide was quenched with 4.7 μl 140 mM BME. To prepare 140 uM BME, 14 M stock was diluted in water 1:100 just before use, and incubated on ice for 30 minutes, then split into 12 μl aliquots and snap-frozen in liquid N2. Blocked ribosomes were stored at −80° C.

Translation:

In Vitro Translation

|  | 1x |
|---|---|
| Solution A | 2.5 |
| Factor Mix | 0.75 |
| Blocked ribosomes | 2.4 |
| mRNA | X |
| UHP | X |
| total | 6.25 |

A molar ratio of about 2:1 mRNA:ribosome (i.e., about 4 μM mRNA) was used. RNA was translated for 30 minutes at 37° C. in a PCR block, and the reaction was stopped directly with MgAc-containing buffer.

Stopping Translation and Rebuffering the Reaction and MBP Target Proteins to Remove Reducing Agent and Free Sulfhydryl Groups To stop and rebuffer the translation reaction, an Amicon 30 k MWCO, 0.5 mL filter was used. The filter was washed with WBT by centrifugation, and the flow through and liquid inside the filter were discarded. 100 μl ice cold WBT and 270 μl WB were pipetted into the rinsed 30 k MWCO filter, which was maintained on ice. The translation reaction was added and resuspended directly in the filter. Five concentration/dilution spins were performed, each for 25 minutes at 7000 g and 4° C. After each spin, the translation reaction was concentrated down to about 40 μl and resuspended with 360 μl WB. After the final 25 minute spin, the translation reaction was concentrated down to about 25 μl. The concentrate was transferred to a PCR tube on ice and resuspended in WB to a final volume of 85 μl.

Rebuffering MBP Target Proteins to Remove Reducing Agent

Amicon 30 k MWCO, 4 ml filters were used. The filters were washed with TBS by centrifugation and the flow through and liquid inside the filter were discarded. MBP stock protein (50 µl) and 4 ml TBS were added, and spun at 4000 g as follows:

1. 15 minute spin, concentrate to 50 µl, resuspend with 4 ml TBS.
2. 15 minute spin, concentrate to 50 µl resuspend with 2 ml TBS.
3. 10 minute spin, concentrate to 50 µl.

After the final spin, the concentrate was transferred to a 1.5 ml tube. The protein was quantified by $A_{280}$ and the concentration was adjusted to 7.5 µM in TBS. For each 20 µl panning reaction, 2 µl was used (0.75 µM final).

5. Ribosome Display:

For panning of the ternary complex, 2 µl MBP target protein (7.5 µM) was mixed with 18 µl of the rebuffered translation reaction in 8-strip PCR tubes. The mix was incubated at 22° C. for 3 hours.

6. Pull-Down of Positive Clones with Streptavidin Paramagnetic Beads:

Preparing the Beads

Original Dynabeads MyOne C1 bead stock (250 µl) were washed 3× in 500 µl WBT, then washed twice for 2 minutes each in Dynabeads solution A (0.1 M NaOH, 50 mM NaCl) for RNAse treatment, and washed three more times in 500 µl WBT. The beads were resuspended in 240 µl at 10 mg/ml. 90 µl of the beads were then resuspended in 500 µl synblock and incubated for 1 hour at RT. Beads were then washed three times in 500 µl WBT, and finally resuspended in 45 µl WBT at 20 mg/µl beads.

Pull-Down

Ten (10) µl (20 mg/ml) of resuspended beads were added to each panning well, and ternary complexes were pulled down at RT for 30 minutes.

7. Washing:

All washing steps were performed at RT with ice cold buffer WBT. Magnetic beads were captured and the supernatants were aspirated with a pipette. Three fast wash steps were performed by adding 100 µl WBT, pipetting to disperse the pellet completely, and capturing the beads. Samples were transferred to new PCR strip tubes after the last wash, and incubated with shaking in 100 µl WBT for 10 minutes in a cold room. Two fast washing steps were repeated, and beads were resuspended in 100 µl WBT, then transferred to new PCR tubes.

8. Reverse Transcription (RT) and PCR on RT:

In Situ Recovery of cDNA

Reverse transcription solutions were prepared as follows. The total reaction volume per panning was 20 µl.

| Solution 1 | |
|---|---|
| pRDV_BbsI_r (10 µM) | 2.5 |
| UHP | 8.5 |
| RNasin Plus | 0.5 |
| µl total | 11.5 |

| Solution 2 | |
|---|---|
| 10x AS buffer | 2.0 |
| DTT (100 mM from kit) | 2.0 |
| dNTP (40 mM total) | 2.0 |
| Affinity Script (AS) | 0.5 |
| µl total | 6.5 |

Solution 1 (11.5 µl) was added to a PCR tube. Magnetic beads from the pulled-down ternary complexes (step 7) were captured and resuspended in 20 µl ice cold WBT. 2 µl of beads were added to Solution A and incubated at 65° C. for 5 minutes in a thermocycler (with a heated lid applied at 65° C.). The mix was cooled to RT and 6.5 µl Solution 2 was added. Samples were then incubated for 1 hour at 50° C. (applying the heated lid at 50° C.) and then for 15 minutes at 70° C. (applying a heated lid at 70° C.).

PCR on RT Using Inner Primers

| | 1x |
|---|---|
| 5x HF buffer | 10 |
| RD_in_for (10 uM) | 2.5 |
| pRDV_BbsI_r (10 uM) | 2.5 |
| dNTPs (10 mM each) | 1.0 |
| RT template | 2.0 |
| Phusion hot start polymerase | 0.5 |
| UHP | 31.5 |
| total | 50 |

| PCR cycling program | |
|---|---|
| 30 sec | 98° C. |
| 10 sec | 98° C. |
| 15 sec | 59° C. |
| 30 sec | 72° C. |
| 5 min | 72° C. |
| ∞ | 4° C. |

Samples were amplified for 10-25 cycles, and analytical samples were taken every 5 cycles for agarose gel electrophoresis.

Buffers and Solutions

| 5x homemade T7 Buffer |
|---|
| 1M Hepes-KOH (pH 7.6) |
| 150 mM magnesium acetate |
| 10 mM spermidine, |
| 200 mM DTT |
| Tris-buffered saline, TBS |
| 50 mM Tris-HCl (pH 7.4) |
| 150 mM NaCl |
| Wash buffer with Tween, WBT |
| 50 mM Tris-HCl (pH 7.4) |
| 150 mM NaCl |
| 50 mM MgAc |
| 0.05% Tween-20 |
| Wash buffer with minimal Tween, WB |
| 50 mM Tris-HCl (pH 7.4) |
| 150 mM NaCl |
| 50 mM MgAc |
| 0.005% Tween-20 |

-continued

Ribosome buffer (w/o 7 mM BME)

20 mM HEPES-KOH pH 7.6
30 mM KCl
10 mM MgAc
Dynalbead wash solution A 100 mM NaOH (DEPC)
50 mM NaCl (DEPC)

Example 2—Construction and Testing of a First Generation DARPin-Based Library

Figure 2:
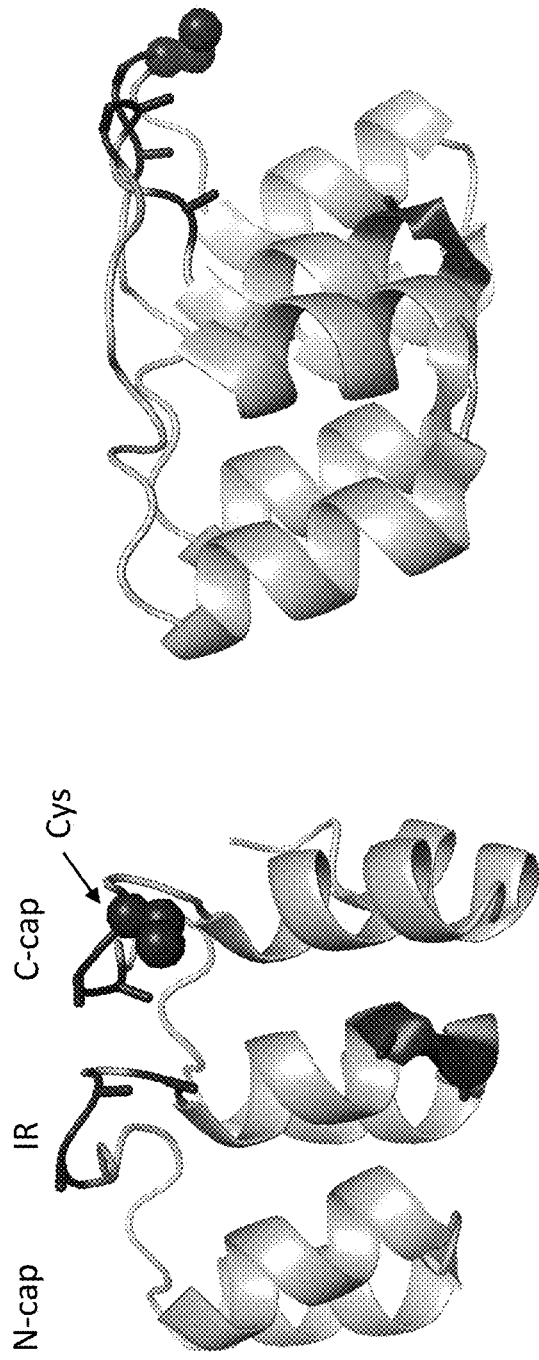
FIG. 2 shows structural models of a designed ankyrin repeat protein (DARPin) scaffold protein designed for a first generation Tethering RD library. The structural models (top) indicate randomized positions within the internal repeat (IR) in darker gray. The cysteine residue for tethering, shown as a space-filled residue, is located in the C-cap region of the protein. Randomized amino acid positions in the structures are shown in black. The corresponding sequences of the N-cap region, the IR, and the C-cap region also are shown (bottom; SEQ ID NOS:1, 2, and 3, respectively). Amino acids at the randomized positions in the IR and the C-cap indicated in bold, and the cysteine tether is underlined. The first position of SEQ ID NO:3 (the C-cap) was Asp or Thr. The theoretical molecular diversity of this library is about $1.2 \times 10^7$.

A combinatorial protein library was designed to include a single Cys residue for tethering the library members to the target. The structure of the DARPin polypeptides in the library is shown in FIG. 2, with the Cys residue located in the C-cap. Sequences of the N-cap region (SEQ ID NO:1), internal repeat (IR; SEQ ID NO:2), and C-cap region (SEQ ID NO:3) also are shown, as are the amino acids located at the randomized positions in the IR and the C-cap. The amino acid at the first position of the C-cap sequence (SEQ ID NO:3) was Asp or Thr.

To construct the DARPin library, a cDNA library encoding DARPins consisting of three ankyrin repeat modules (N1C library) was cloned. The N-terminal capping repeat was followed by one IR encoding randomized amino acid positions for target binding, which was capped by a C-terminal repeat featuring a cysteine (Cys) residue for tethering. Sequence diversity was encoded in the IR and also adjacent to the Cys tether in the C-cap, creating a DARPin library of $1 \times 10^7$ individual sequence variants. Specifically, each "X" position in the IR (SEQ ID NO:2) was Ala, Glu, Gly, Lys, Leu, Met, Pro, Gln, Arg, Ser, Thr, Val, or Trp, in a random fashion, and the "X" in the second position of the C-cap sequence (SEQ ID NO:3) was Ala, Asp, Glu, Phe, Gly, His, Lys, Leu, Asn, Gln, Arg, Ser, Thr, Val, Trp, or Tyr. These positions were encoded on the DNA level by the degenerate codon NNG, where N stands for any of the four nucleotides (A, C, G, T).

Maltose binding protein (MBP) from *Escherichia coli* was used as a model target protein, with a single Cys introduced at one of several different surface-exposed positions (position 211, 233, 337, or 352) by site-directed mutagenesis. The redox state of the Cys side chain in each recombinantly expressed MBP mutant was verified by ESI-LC/MS.

Figure 3:
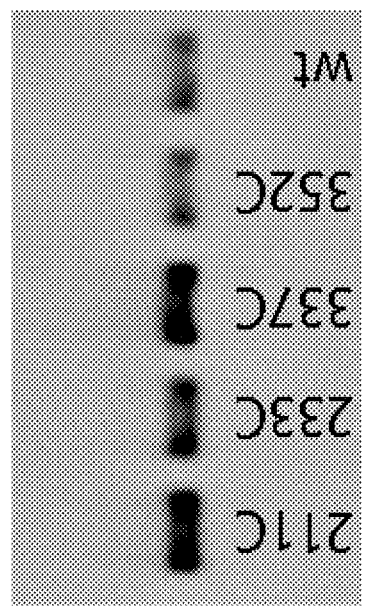
FIG. 3 is a picture of a gel showing enrichment of selected DARPin pools interacting with different MBP targets. After panning the naïve DARPin library against five different MBP targets using the optimized conditions of Tethering-RD, selected mRNA pools were reverse transcribed and amplified by PCR, giving rise to the bands shown. With the exception of target 352C, the bands on the agarose gel show stronger enrichment of DARPins panned against Cys containing targets than wild-type MBP, indicating Cys-dependent, site-specific enrichment.

For RD, the PURExpress system (New England Biolabs; Ipswich, Mass.) was used, with modification of several steps in a standard RD selection method (Example 1; Zahnd, *Nat. Methods* 4:269-279, 2007) to allow for tethering to occur via disulfide bond formation. Experimental conditions were successfully established to enable panning and selection of DARPins by Tethering-RD. When panning the naïve, tethering-competent N1C DARPin library against a variety of Cys point mutants of MBP, stronger enrichment of DARPin clones was observed for the mutant targets than for Cys-free, wild-type MBP (FIG. 3). Pools of selected DARPins were analyzed by next generation sequencing to identify clones that bound MBP in a site-specific mode defined by the Cys position in the target.

Although the initial results shown in FIG. 3 suggest otherwise, a detailed bioinformatic analysis of the selected pools by NGS sequencing did not yield evidence for either positively enriched single DARPin clones, or for the formation of disulfide bonds during the panning step. This may be resolved by performing additional, more stringent selections to further enrich true binding sequences.

Example 3—Construction and Testing of a Second Generation Peptide-Based Library

Figure 6:
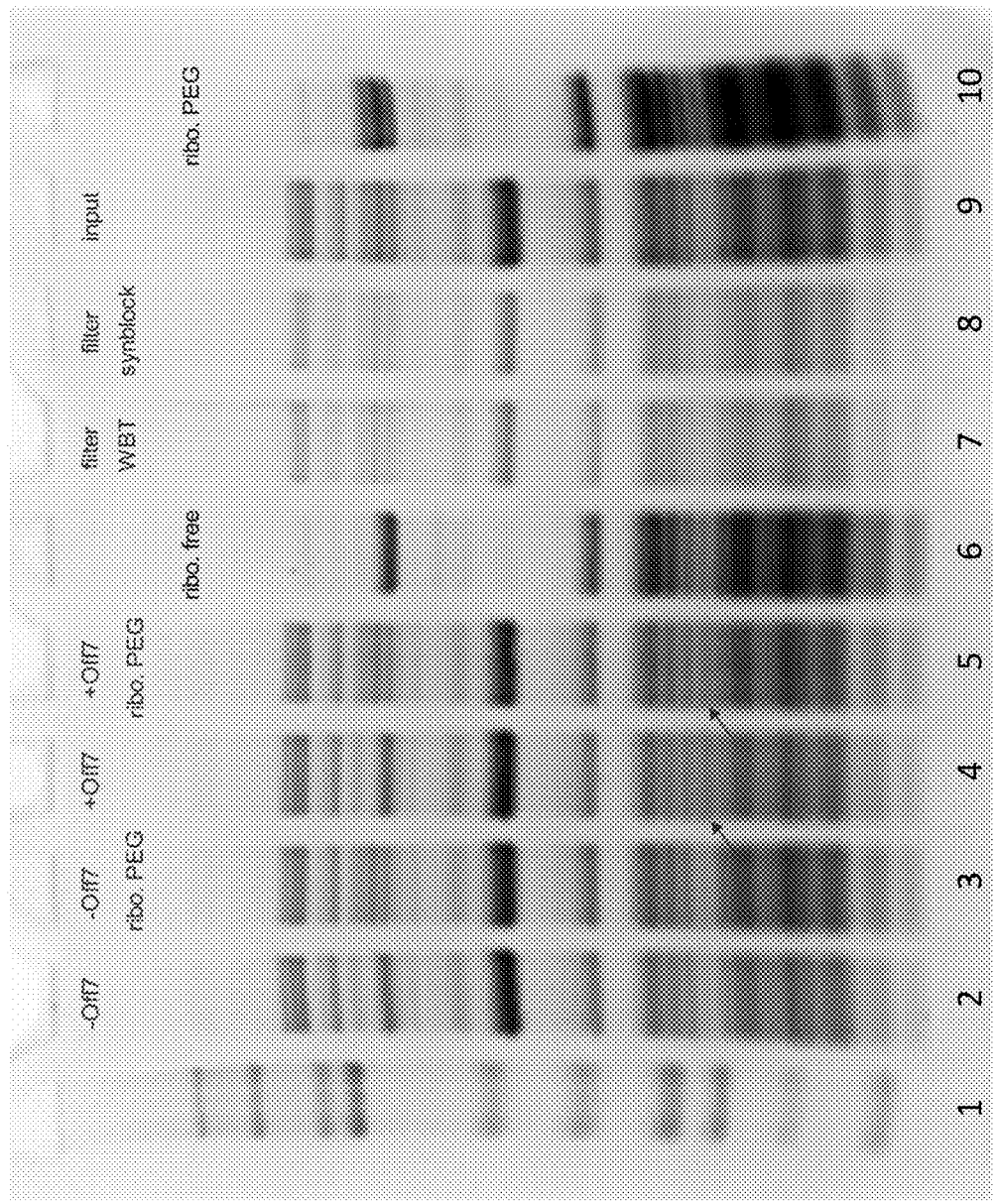
FIG. 6 is a picture of a gel showing that ribosomes blocked with malPEG (ribo.PEG) retain their full ability to translate protein. A plasmid expressing the DARPin protein Off7 (arrows, ~20 kDa) was expressed at the same levels when the IVTT reaction contained non-modified or modified ribosomes (lanes 4 and 5). Control lanes 2 and 3 contain no plasmid and show several bands corresponding to ribosomal proteins, which shift to higher molecular weight as a result of the cysteines on these proteins reacting with of malPEG. Lanes 6 and 10 contain unmodified and blocked ribosomes, respectively. Several bands shifted to higher molecular weight as a result of blocking with malPEG.

In further studies, the method of Example 2 are modified in one or more of the following aspects:
(a) replacement of the DARPin library with a peptide-based library (FIG. 4);
(b) increasing the concentration of MBP target used in the panning step;
(c) removal of excess reducing agent and other small molecular weight sulfhydryl groups after the translation step and before panning the library against the target, using diafiltration of translated ternary ribosomal complexes;
(d) blocking of free Cys residues on the surface of the ribosomes to block them from participating in the formation of non-specific disulfide bonds (FIGS. 5 and 6);
(e) modification of the experimental conditions for the panning step and pull-down of positive ternary complexes bound to the target by the disulfide tether (FIGS. 7 and 8); and
(f) increasing the number of rounds of RD performed.

While items (a) through (e) might reduce limitations on formation of tethered, positive ternary complexes, the modified pull-down step in item (e) and the addition of multiple experimental enrichment rounds in item (f) should promote the enrichment of tether formation.

A second generation Tethered RD library was developed using a randomized, 9-amino acid peptide library with a Cys located near the C terminus of the randomized sequence (specifically, separated by two glycine residues from the randomized positions as shown in FIG. 4). This library had a much higher diversity and a more flexible Cys anchor point than the DARPin library. The peptide library was cloned and sequence verified.

Increasing the concentration of the target protein in the panning step of a Tethered RD protocol can increase the rate of formation of the critical tether between the displayed polypeptides and the target. The amount of target protein in a panning step typically is limited by several factors, including the requirement to provide matching amounts of immobilized affinity support (immobilized streptavidin to bind biotin) to pull down both tethered and non-tethered target following the panning step. In the studies of Example 2, a 0.75 µM target concentration and streptavidin magnetic beads were used for the pull-down. These are standard experimental settings for capturing biotinylated targets. Increasing the target concentration of Cys-containing, biotinylated targets, however, increases the chance of forming disulfide bond-linked target dimers that feature two biotin moieties, which may act as efficient cross linkers of individual paramagnetic beads and result in their aggregation. Such aggregated beads may occlude the available streptavidin sites for efficient target pull-down, and may also trap non-tethered ternary complexes inside the aggregates, increasing the recovery of non-specifically bound clones with negative effects on overall enrichment.

To resolve these problems, conditions were developed that allow for up to 50-fold increase of the target concentration (to 30-40 µM) while circumventing the issues noted above. For example, following the panning step, high capacity streptavidin-SEPHAROSE® beads (34 µm diameter beads with covalently immobilized streptavidin) are used to selectively sequester the free target but not the target tethered to ternary complexes. The supernatant containing both tethered and non-tethered ternary complexes is then treated with streptavidin magnetic beads to pull down the positive ternary complexes and separate them from non-tethered complexes. A key to providing a large binding capacity for the ~50 kDa targets while prohibiting the binding of the 2 MDa ternary complexes is to partially pre-block the streptavidin-SEPHAROSE® beads on their surface with free biotin. By selectively pre-blocking streptavidin sites near the surface of the beads, free biotinylated targets (including target dimers) can be absorbed into the core of the beads while the 2 MDa ternary complexes, which can only diffuse into the outer shell of a SEPHAROSE® bead due to its molecular weight exclusion limit, are prohibited from binding and remain in the supernatant. FIGS. 7A and 7B show the binding of MBP target to beads that are not blocked (FIG. 7A) or that are semi-blocked (FIG. 7B, 60% of streptavidin sites blocked with biotin). Streptavidin sites in the outer shell of the beads are blocked, revealing the desired concentric pattern of surface blockage. FIGS. 8A-8D demonstrate that ternary complexes displaying a biotinylated sfGFP fusion protein do bind to non-blocked beads (FIG. 8A), but bind less to semi-blocked beads (FIG. 8B). When the supernatants of these samples were subsequently incubated with non-blocked beads, the supernatant of the semi-blocked beads showed a stronger presence of the desired ternary complexes, as evidenced by the stronger pull-down signal in FIG. 8D compared to FIG. 8C.

In addition, maleimide-dPEG4-(m-dPEG$_{11}$)$_3$ (malPEG; FIG. 5) was used to block the free surface cysteines on the ribosomes. malPEG is a branched molecule that can increase the hydrodynamic radius of the molecule to limit its reactivity toward sulfhydryls located in the core of the ribosome. As shown in FIG. 6, ribosomes that were blocked with malPEG (ribo.PEG) retained their full ability to translate protein. A plasmid expressing the DARPin protein Off7 (arrows, ~20 kDa) was expressed at the same levels when the IVTT reaction contained non-modified ribosomes (lane 4) or modified ribosomes (lane 5). Controls without the Off7-encoding plasmid showed several bands corresponding to ribosomal proteins (lanes 2 and 3), which shifted to higher molecular weight as a result of the cysteines on these proteins reacting with malPEG. The samples in lanes 6 and 10 contained unmodified and blocked ribosomes, respectively, and demonstrate that several bands shifted to higher molecular weight as a result of blocking with malPEG.

Figure 9:
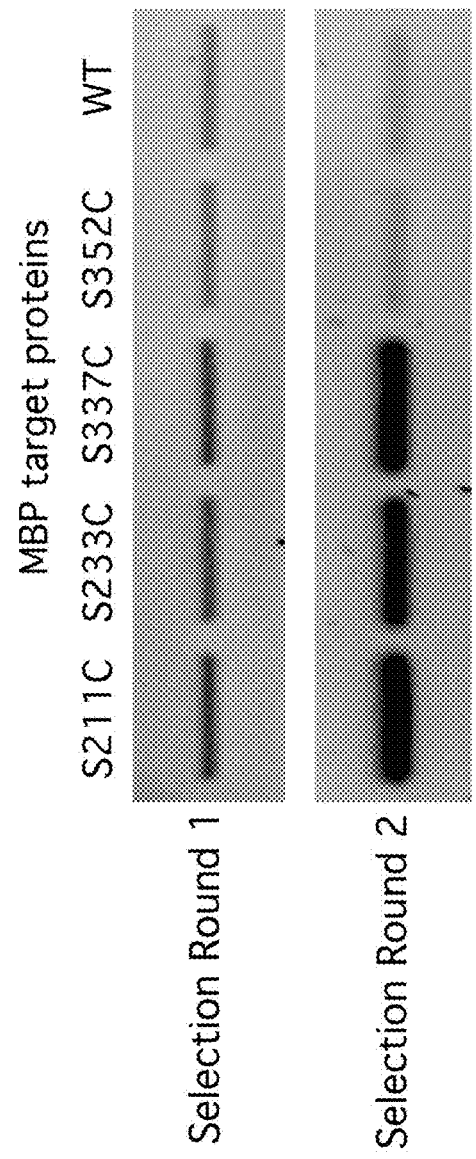
FIG. 9 is a picture of a gel showing enrichment of selected peptide pools interacting with different MBP targets after two rounds of RD selection. After panning the naïve peptide library ($3 \times 10^{11}$ theoretical molecular diversity) for one and two rounds against four different mutant MBP targets (single point cysteine mutants) and WT MBP (WT) using the optimized conditions of Tethering-RD, selected mRNA pools were reverse transcribed and amplified by PCR, giving rise to the bands shown. With the exception of target S352C, the bands on the agarose gel show stronger enrichment of peptides panned against Cys containing targets than WT MBP, indicating Cys-dependent, site-specific enrichment.

Further, experiments were conducted to determine the effect of increasing the number of rounds of RD. After panning the naïve peptide library ($3 \times 10^{11}$ theoretical molecular diversity) for one round or two rounds against four different mutant MBP targets (single point cysteine mutants) and WT MBP (WT) using optimized Tethering-RD conditions, selected mRNA pools were reverse transcribed and amplified by PCR. As shown in FIG. 9, peptides panned against the Cys containing MBP targets S211C, S233C, and S337C were strongly enriched after two rounds, as compared to WT MBP and the S352C target. Thus, Cys-dependent, site-specific enrichment can be achieved by increasing the number of RD rounds.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for enriching for a molecule that binds to a target molecule, comprising:

(a) contacting the target molecule with a population of candidate binding partners, wherein each candidate binding partner is coupled to a different nucleic acid tag, wherein each candidate binding partner further comprises or is coupled to a first tethering partner, wherein the target molecule is coupled to a second tethering partner, and wherein the first and second tethering partners interact and promote binding between the target molecule and a candidate binding partner that binds to the target molecule; and (b) separating at least one candidate binding partner bound to the target molecule from candidate binding partners not bound to the target molecule.

2. The method of claim 1, wherein the population of candidate binding partners comprises polypeptides.

3. The method of claim 1, wherein the population of candidate binding partners comprises nucleic acids.

4. The method of claim 1, wherein the population of candidate binding partners comprises aptamers.

5. The method of claim 1, wherein the population of candidate binding partners comprises small molecules.

6. The method of claim 1, wherein the nucleic acid tag is a DNA tag.

7. The method of claim 1, wherein the nucleic acid tag is a DNA tag, and wherein the method further comprises using the sequence of the DNA tag to identify the at least one candidate binding partner.

8. The method of claim 1, wherein the nucleic acid tag is an mRNA tag.

9. The method of claim 1, wherein the nucleic acid tag is an mRNA tag, and wherein the method further comprises using reverse transcription of the mRNA tag and sequencing cDNA resulting from the reverse transcription to identify the at least one candidate binding partner.

10. The method of claim 1, wherein the first tethering partner is a first cysteine residue within each candidate binding partner, the second tethering partner is a second cysteine residue within the target molecule, and wherein the first and second cysteine residues interact to form a disulfide bond when a candidate binding partner has affinity for the target molecule.

11. The method of claim 1, wherein the first tethering partner is a first biomolecule coupled to the candidate binding partners and the second tethering partner is a second biomolecule coupled to the target molecule, and wherein the first and second tethering partners interact when a candidate binding partner has affinity for the target molecule.

12. The method of claim 1, wherein the first tethering partner is a first synthetic molecule coupled to the candidate binding partners and the second tethering partner is a second synthetic molecule coupled to the target molecule, and wherein the first and second tethering partners interact when a candidate binding partner has affinity for the target molecule.

13. The method of claim 1, further comprising using a display technique.

14. The method of claim 13, wherein the display technique comprises ribosome display.

15. The method of claim 13, wherein the display technique comprises mRNA display, phage display, covalent DNA display, CIS display, STABLE, or microbead display.

16. The method of claim 1, wherein the target molecule is a polypeptide.

17. The method of claim 16, wherein the polypeptide has a length of 10 to 50 amino acids.

18. The method of claim 16, wherein the polypeptide has a length of 50 to 100 amino acids.

19. The method of claim 1, further comprising separating target molecules tethered to a candidate binding partner from target molecules not tethered to a target molecule.

20. The method of claim 19, wherein the target molecules are biotinylated, and wherein the further separating comprises contacting the biotinylated target molecules with streptavidin-conjugated beads.

* * * * *